United States Patent [19]

Hench et al.

[11] 4,171,544

[45] Oct. 23, 1979

[54] BONDING OF BONE TO MATERIALS PRESENTING A HIGH SPECIFIC AREA, POROUS, SILICA-RICH SURFACE

[75] Inventors: Larry L. Hench, Gainesville, Fla.; Michael M. Walker, Troy, N.Y.

[73] Assignee: Board of Regents, for and on behalf of the University of Florida, Tallahassee, Fla.

[21] Appl. No.: 893,792

[22] Filed: Apr. 5, 1978

[51] Int. Cl.$^2$ .................. A61F 1/24; A61B 17/18; C03C 3/04; C03C 3/22

[52] U.S. Cl. .......................... 3/1.9; 3/1.912; 128/92 C; 128/92 B; 128/92 D; 32/10 A; 106/52; 106/40 R; 156/89; 156/325

[58] Field of Search .............. 106/52, 54, 40 R, 40 V, 106/39.6, 89, 85; 3/1.9, 1.91–1.913; 32/10 A; 128/92 C, 92 CA, 92 B, 92 D

[56] References Cited

U.S. PATENT DOCUMENTS

| | | | |
|---|---|---|---|
| 3,054,221 | 9/1962 | Elmer | 106/52 |
| 3,147,127 | 9/1964 | Shannon | 106/99 |
| 3,804,647 | 4/1974 | Elmer et al. | 106/52 |
| 3,908,201 | 9/1975 | Jones et al. | 3/1.4 |
| 3,919,723 | 11/1975 | Heimke et al. | 106/73.5 |
| 3,922,155 | 11/1975 | Broemer et al. | 106/39.6 |
| 3,923,533 | 12/1975 | Hammel et al. | 106/52 |
| 3,987,499 | 10/1976 | Scharbach | 3/1.91 |
| 4,031,571 | 6/1977 | Heimke et al. | 3/1.913 |
| 4,039,339 | 8/1977 | Elmer et al. | 106/54 |
| 4,056,399 | 11/1977 | Kirkpatrick et al. | 106/69 |

FOREIGN PATENT DOCUMENTS

1477899 6/1977 United Kingdom.
1505815 3/1978 United Kingdom.

OTHER PUBLICATIONS

Hench et al., "Bonding Mechanisms . . . Prosthetic Materials", J. Biomed. Mater. Res. Symp., No. 2 (Part I) pp. 117–141 (1971).
Hench et al., "Direct Chemical Bond . . . Bone and Muscle", J. Biomed. Mater. Res. Symp, No. 4, pp. 25–42 (1973).
Hench et al., "Histochemical Responses . . . Interface", J. Biomed. Mater. Res. Symp., No. 5, (Part I), pp. 49–64 (1974).
Clasck et al., "The Influence of Surface Chemistry . . . Implant Material Selection", J. Biomed. Mater. Res., vol. 10, pp. 161–174 (1976).

*Primary Examiner*—O. R. Vertiz
*Assistant Examiner*—Mark Bell
*Attorney, Agent, or Firm*—Dennis P. Clarke

[57] ABSTRACT

Compositions possessing a porous, high specific area, silica-rich surface, or capable of developing such a surface in vivo, form strong bonds with bone tissue. These compositions are thus excellent materials for dental and surgical implants, or the coatings thereof. Examples of such compositions include highly porous glasses and glass-ceramics comprising at least about 80 weight percent silicon dioxide, hardened inorganic cements such as Portland cement and known silicon dioxide-based biologically active glasses and glass-ceramics. Neither calcium, sodium nor phoshorus compounds are necessary ingredients. Cements which develop the above described surface characteristics in vivo form a strong bond with both bone and implant when used in the fixation of dental and surgical implants, especially those made or coated with a biologically active silicon dioxide-based glass or glass-ceramic.

13 Claims, No Drawings

BONDING OF BONE TO MATERIALS PRESENTING A HIGH SPECIFIC AREA, POROUS, SILICA-RICH SURFACE

BACKGROUND OF THE INVENTION

Biologically active silicon dioxide (silica)-based glasses and glass-ceramics are known to the art. These materials are characterized by their ability to form a direct chemical bond of excellent strength with bone in vivo. The bond strength is not strongly dependent upon the degree of crystallinity of the biologically active material. However, the use of a partially or fully crystallized glass-ceramic is often preferred because devitrification increases the strength of the biologically active material itself. It has been proposed to construct a variety of dental and surgical implants for cement-free implantation from these biologically active glasses and glass-ceramics and of stronger materials such as aluminum oxide and surgical implant alloys coated therewith. The silica-based biologically active glasses and glass-ceramics of the prior art generally contain about 40 to 60 weight percent silica as the network former plus substantial levels of soluble modifiers such as sodium oxide, potassium oxide, calcium oxide, magnesium oxide, phosphorus pentoxide, lithium oxide and calcium fluoride. Boron oxide may be substituted for some of the silicon dioxide. A particularly preferred composition of the prior art, designated as composition 45S5, contains 45 weight percent silicon dioxide, 24.5 weight percent sodium oxide, 24.5 weight percent calcium oxide, and 6 weight percent phosphorus pentoxide. The chemical bond between a biologically active glass or glass-ceramic material and bone is to be distinguished from the mechanical type of bond formed by the ingrowth and interlocking of bone tissue within a macroscopically porous implant surface. Until now, it has been generally believed that a biologically active glass or glass-ceramic material possesses its activity because of its surface reactivity in physiological solutions. That is, soluble ions such as the sodium and calcium ions are selectively leached from the glass or glass-ceramic material, thereby causing the surrounding physiological fluid to become more alkaline. The alkaline solution then attacks the glass or glass-ceramic material, forming a silica gel layer thereon. It is to this silica gel layer, according to this proposed mechanism, that the fresh growing bone bonds [Hench, L. L., Splinter, R. J., Allen, W. C. and Greenlee, T. K., J. Biomed. Mater. Res. Symp., No. 2 (Part I), pp. 117–141 (1971); Hench, L. L. and Paschall, H. A., J. Biomed. Mater. Res. Symp., No. 4, pp. 25–42 (1973); Hench, L. L. and Paschall, H. A., J. Biomed. Mater. Res. Symp., No. 5 (Part I), pp. 49–64 (1974); Piotrowski, G., Hench, L. L., Allen W. C. and Miller, G. J., J. Biomed. Mater. Res. Symp., No. 6, pp. 47–61 (1975); Clark, A. E., Hench, L. L. and Paschall, H. A., J. Biomed. Mater. Res., 10, pp. 161–174 (1976); U.S. Pat. Nos. 3,919,723; 3,922,155; 3,981,736; 3,987,499; 4,031,571].

It is of course known to achieve the fixation of dental or surgical implants to the bone of the recipient by utilizing organic resin cements such as polymethylmethacrylate. However, there are known disadvantages in the use of such cements related to reactivity in vivo, toxicity, and loosening of the fixation. It is also known to strengthen an implant resin cement by incorporating therein various types of reinforcing material including particles of glass (see e.g. U.S. Pat. No. 3,919,773). Glass reinforced hardened inorganic cements (e.g. Portland cement) are also known (see U.S. Pat. No. 3,147,127).

Summary of the Invention

A novel dental or surgical implant having a surface for bonding to the bone of a recipient has now been discovered in which said bonding surface comprises a biologically compatible glass, glass-ceramic or ceramic material comprising at least about 80 weight percent silicon dioxide and having a specific surface area of at least about 80 square meters per gram, a porosity of from about 10 to about 50 volume percent, and an average pore diameter of from about 20 to about 300 Angstroms.

The present invention also includes a dental or surgical implant having a surface for bonding to the bone of a recipient in which said bonding surface comprises a biologically compatible inorganic material of adequate physical characteristics for the intended use, other than a silicon dioxide—based glass or glass-ceramic containing less than about 80 weight percent silicon dioxide, that is capable of developing a porous silica-rich surface layer having a specific surface area of at least about 80 square meters per gram within about 10 days' exposure to aqueous tris(hydroxymethyl)aminomethane buffer at a pH of 7.2 and a temperature of 37° C. Materials contemplated within this second aspect of the invention include certain ceramics and hardened inorganic cements, e.g., Portland cement.

Additionally, the present invention includes an improvement to a process for fixing a dental or surgical implant to bone comprising placing a wet cement between the surface of the bone and implant and allowing said cement to harden. Said improvement comprises using a biologically compatible inorganic cement which, in the hardened state, is capable of developing a porous silica-rich surface layer having a specific surface area of at least about 80 square meters per gram within about 10 days' exposure to aqueous tris(hydroxymethyl)aminomethane buffer at a pH of 7.2 and a temperature of 37° C. Portland cement is one inorganic cement which may be used. In a preferred embodiment of this improvement, the wet cement is mixed with particles of a biologically active silicon dioxide—based glass or glass-ceramic. In another preferred embodiment, the bonding surface of said implant in contact with said inorganic cement comprises a biologically active silicon dioxide—based glass or glass-ceramic.

DETAILED DESCRIPTION OF THE INVENTION

We have now surprisingly discovered that biologically active silica-based glass and glass-ceramic materials fabricated by standard casting and crystallization techniques bond strongly to bone by virtue of their ability to develop in vivo a porous silica-rich surface layer *having at least a minimum specific surface area.* Silica-based glass and glass-ceramic materials which do not develop a surface layer in vivo with the above characteristics generally form poor chemical bonds, or none at all, with bone. The high area silica-rich surface layer (roughly about 25 to 100 microns thick) apparently provides a vast number of sites for deposition and interaction of various of the organic and inorganic components of healing bone. In vivo biological activity may be predicted by a convenient in vitro test. Thus, a silica-based glass or glass-ceramic will bond strongly to bone in vivo if it is capable of developing a porous silica-rich surface layer having a specific surface area of at least about 80 square meters per gram of said layer within about ten days' exposure to aqueous tris(hydroxymethyl)aminomethane buffer at a pH of 7.2 and a temperature of 37° C.

Table I presents data on a series of non-porous glasses of the silicon dioxide-calcium oxide-sodium oxide-phosphorus pentoxide system. Biological activity is strongly dependent upon silicon dioxide content, but less dependent upon the contents of the other three components. For a calcium oxide: sodium oxide weight ratio of about 0.4 to about 2.5 and a phosphorus pentoxide content of 6 weight percent, the boundary line of biological activity was observed to fall between about 54 and 58 weight percent silicon dioxide. This boundary range drops to about 45 to 55 weight percent silicon dioxide when phosphorus pentoxide is eliminated. Replacement of sodium oxide by potassium oxide has little effect on biological activity. Silicon dioxide-sodium oxide glasses containing more than about 78 weight percent silicon dioxide did not bond to bone. Neither did essentially pure silicon dioxide glass. The glasses of Table I were prepared by melting a mix of reagent grade calcium, sodium and potassium carbonates, phosphorus pentoxide and 5 micron silicon dioxide powders at about 1200°–1500° C., casting disc shaped samples and then annealing said samples at about 450°–700° C. 4×4×1 mm. implants were then prepared for the rat tibial mini push out test for in vivo bonding to bone described below. Table I shows the strong dependence of biological activity on surface area developed in vitro. Thus, if a non-porous glass of this system contains too much $SiO_2$, it will not be able, as indicated by the in vitro test, to develop an adequate surface layer in vivo to bond to bone. The surface area numbers were obtained by the B.E.T. nitrogen adsorption method on critical point ($CO_2$) dried glass samples and are expressed as times increase. Independent direct measurements of surface area indicate that a 1,000-fold surface area increase for the total sample is equivalent to generation of a specific surface area of about 80 square meters per gram of dry surface layer material.

Table I

| Non-porous Glass Composition (wt. %) | | | | | In vivo Bonding to Bone[a] | Surface Area Increase (B.E.T.)[b] |
|---|---|---|---|---|---|---|
| $SiO_2$ | CaO | $Na_2O$ | $P_2O_5$ | $K_2O$ | | |
| 53.8 | 27.6 | 12.2 | 6.4 | 0 | + | 1100 |
| 53.6 | 20.2 | 20.2 | 6.0 | 0 | + | 7060 |
| 53.0 | 12.8 | 28.0 | 6.3 | 0 | + | 9130 |
| 41.1 | 26.4 | 26.5 | 6.0 | 0 | + | 16,800[c] |
| 45.0 | 24.5 | 24.5 | 6.0 | 0 | + | 31,300 |
| 47.9 | 23.0 | 23.1 | 6.0 | 0 | + | 10,800[c] |
| 50.8 | 21.6 | 21.6 | 6.0 | 0 | + | 5930[c] |
| 58.4 | 17.8 | 17.8 | 6.0 | 0 | − | 200 |
| 58.7 | 25.1 | 9.8 | 6.4 | 0 | − | < 20[g] |
| 57.8 | 10.4 | 25.5 | 6.3 | 0 | − | 860 |
| 45.0 | 24.5 | 30.5 | 0 | 0 | + | 27,100 |
| 55.4 | 21.2 | 23.4 | 0 | 0 | − | 130[c] |
| 39.9 | 21.8 | 0 | 5.3 | 33.0 | + | 59,700 |
| 59.3 | 0 | 40.7 | 0 | 0 | [d] | < 20[g] |
| 73.6 | 0 | 26.4 | 0 | 0 | ± | < 20[g] |
| 78.3 | 0 | 21.7 | 0 | 0 | − | < 20[g] |
| 83.0 | 0 | 17.0 | 0 | 0 | − | < 20[g] |
| 100 | 0 | 0 | 0 | 0 | − | < 20[g] |
| ~70[e] | ~10[e] | ~20[e] | 0 | 0 | − | < 20[g] |
| 48.3 | 18.9[f] | 26.4 | 6.4 | 0 | − | 18,300[c] |

[a] 30 days after implantation
[b] after 10 days exposure in vitro to aqueous tris(hydroxymethyl)aminomethane buffer at a pH of 7.2 and a temperature of 37° C.
[c] 24 hours in vitro
[d] implant dissolved in vivo
[e] standard soda-lime-silicate microscope slide (Corning Glass Works, Corning, New York) - nominal composition given
[f] MgO substituted for CaO
[g] Based on lower limit of sensitivity of BET MACHINE (.01m²)

The presence or absence of bonding with bone was determined using the known rat tibial mini push out test. This test utilizes the following procedure. Implants of dimensions 4×4×1 mm are fabricated for each composition tested. Each is wet polished using 180, 320 and 600 grit silicon carbide polishing discs. A final dry polishing with a 600 grit disc is followed by ultrasonic cleaning in reagent grade acetone for two minutes. The implants are then wrapped in surgical drapes and gas sterilized with ethylene dioxide. Male Sprague-Dawley rats in the 150 to 300 g mass range are used as the test animal. Sodium pentabarbital is administered intraperitoneally to anesthetize the animal. A quantity of 0.1 cc atropine is injected subcutaneously to prevent bronchial congestion. An incision is made on the anterior surface of the left hind leg from the knee to midway down the tibia. The peroneal muscles on the lateral aspect of the tibia are cut away from the bone at their origin. The anterior tibialis and common extensors are separated from the medial portion of the tibia. A Hall II drill driven by compressed nitrogen gas with a carbide tip dental burr is used to form a slot in the lateral and medial cortices of the anterior border of the tibia. The implants are inserted into this defect and the incision closed. The relative dimensions of the implant and the tibia are such that the implant protrudes slightly on either side of the tibia after implantation. Testing for bonding with bone 30 days after implantation provides a reliable test for bonding ability. After sacrifice, the test tibiae are excised from each animal and cleaned of adhering soft tissues. The area over the exposed ends of each implant is examined and cleaned of boney overgrowths. This is done to prevent undue mechanical interference. The mechanical integrity of the bond is then tested. Modified sponge forceps are used to apply a push out load of approximately 30 Newtons onto the implant. If the implant resists dislodgement under the applied load, then it is deemed to have passed the mini push out test for bonding. If any movement is observed between the implant and the surrounding bone, then it is considered to have failed the bond test.

Even more surprising is the discovery that bone bonds strongly to any inorganic biologically compatible material, including but not limited to silicon dioxide—based glasses and glass-ceramics, that either possesses before implantation a porous silica-rich surface layer having at least a minimum specific surface area or develops a surface layer in vivo of the above nature. The unifying characteristic of these biologically active (i.e., capable of forming a strong chemical bond in vivo with bone) materials is the availability to the growing bone of the required high surface area, porous, silica-rich surface layer. Except to the extent that soluble modifiers may contribute to the development in vivo of the requisite surface layer, neither calcium, sodium nor phosphorus compounds are necessary ingredients in a biologically active material. Biological activity may be predicted by B.E.T. nitrogen adsorption analysis of the material itself or, if the requisite surface layer is developed in vivo, of a sample treated according to the in vitro test described above. The surface area is expressed herein in units of square meters per gram of surface layer material on a dry basis. A surface area of 80 square meters per gram may be developed, depending on the material tested, within as little as six hours. When a biologically active material contains both soluble calcium ions and soluble ions containing phosphorus and oxygen, calcium phosphate or related compounds may deposit quickly upon the outermost portions of the silica-rich surface layer both in vivo and in the in vitro test described above. This deposition is generally formed from ions generated by the biologically active material itself and appears to benefit in vivo activity. The presence of such a deposition does not substantially affect the results of B.E.T. analysis in terms of increase in surface area after reaction.

As defined in this application the term glass refers to a primarily vitreous inorganic material, while the term glass-ceramic refers to a glass which is from about 20 to 100 volume percent devitrified. The term cement refers to a composition which may be used to fasten different articles together by virtue of its ability to harden. The term ceramic refers to a polycrystalline ceramic material other than a glass-ceramic.

It is important to distinguish the chemical bond between bone and a biologically active material from the mechanical bond caused by the interlocking of growing bone tissue within large (about 10 to 200 microns) surface pores of certain known implant materials. The direct chemical bond with bone of the biologically active materials described herein is caused by chemical forces, and is defined broadly to include primary (e.g., ionic, covalent, epitaxial) and secondary (e.g., van der Waals, hydrogen bond, London dispersion force) chemical bonds. The porosity of the requisite silica-rich surface layer is of a different nature from that existing in implants relying on a mechanical interlock for bonding to bone. For substantial growth of hard tissue to occur a pore diameter of at least about 50 microns is required. In the present invention however the active silica-rich surface layer generally has pore diameters no larger than about 3,000 Angstroms, which is too small for substantial ingrowth of growing bone tissue to occur. The present invention is thus not subject to the known disadvantage of mechanical interlock into a porous substrate, i.e. the strength reduction resulting from the void fraction left unoccupied by the growing bone.

As used in this application the term dental implants refers to, for example, artificial teeth, crowns, inlays, etc. The term surgical implants refers to bone pins, bone plates, bone replacement prostheses, prosthetic devices such as hip and other joint prostheses, or any other surgical implant or prosthesis which must be bound directly to the bone of the recipient. It will of course be required that the biologically active material employed in any particular instance be biologically compatible and have adequate physical characteristics, such as strength, abrasion resistance, fatigue resistance, elastic modulus, ductility, etc., for the intended use. As used in this application the term biologically compatible means that the material is benign or non-toxic in the in vivo biological system in which it is to be employed, and does not adversely interfere with the bone growth process. The last entry in Table I shows that, at least in certain circumstances, replacement of calcium oxide with magnesium oxide can render a silica-based material biologically incompatible, possibly because the Ca:Mg ratio in the surrounding body fluids is substantially altered.

The entire bonding surface of an implant, i.e. the surface in contact with the bone of the recipient for bonding thereto, must be biologically compatible. In some cases, however, some of said bonding surface may be biologically compatible but inactive. Thus, for example, the scope of the present invention includes an implant made of or coated with a phase-separated glass or glass-ceramic material, with both active (high surface area developed in vivo) and inactive (low surface area developed in vivo) regions present, even though the overall average of the specific surface area developed in vitro by such a material may be less than about 80 square meters per gram. The present invention also includes an implant wherein a portion of the surface thereof in contact with the bone of the recipient is, e.g., a biologically compatible but inactive metal or ceramic.

As one aspect of the invention described herein the bonding surface of a dental or surgical implant comprises a biologically compatible glass, glass-ceramic or ceramic material comprising at least about 80 weight percent silicon dioxide and having a specific surface area of at least about 80 square meters per gram, a porosity of from about 10 to about 50 volume percent and an average pore diameter of from about 20 to about 300 Angstroms, with some pores being as large as about 3,000 Angstroms in diameter. It is to be noted that the indicated surface properties are present in the surface material itself before in vivo implantation. Thus, it is not necessary that the material be surface reactive or subject to preferential leaching in physiological solutions. This observation is quite surprising and unexpected. The advantages of using a glass, glass-ceramic or ceramic of this aspect of the invention are low cost and the fact that only low amounts (or virtually none) of ionic materials are leached into the body from such a material. It is not necessary that the materials of this aspect of the invention contain compounds of either calcium or phosphorus. Therefore, one group of said materials consists of those containing, on an elemental basis, less than about 1 weight percent calcium and less than about 0.1 weight percent phosphorus. Another group of said materials consists of those comprising at least about 95 weight percent silicon dioxide, less than about 1 weight percent calcium and less than about 0.1 weight percent phosphorus. In another embodiment said material, preferably a glass, comprises at least about 80 weight percent silicon dioxide and up to about 20 weight percent boron oxide. An example of a useful biologically active material is Thirsty Glass (Corning Glass Works, Corning, N.Y.) a highly porous glass consisting essentially of silicon dioxide and boron oxide. Thirsty Glass is the acid leached product of the original phase separated borosilicate glass from which it is made.

A surgical or dental implant of the aspect of the invention under discussion may be a unitary glass, glass-ceramic or ceramic implant, or comprised of a substrate material coated with the biologically active material, or possess any other known type of configuration. Known methods of casting, crystallizing and sintering may be employed to make unitary implants such as artificial teeth. When greater strength is needed than would be provided by the biologically active material per se, known methods of coating a metal (e.g. Vitallium, trademark of Howmedica Inc., New York, N.Y.), non-biologically active ceramic or other substrate may be employed, such as firing techniques, immersion techniques, application plus sintering techniques, flame spraying, etc. A particularly advantageous method of coating an alumina substrate with a biologically active glass or glass-ceramic is disclosed in the commonly assigned pending U.S. patent application Ser. No. 766,749, now U.S. Pat. No. 4,103,002. A particularly advantageous method of coating an alloy substrate with a biologically active glass or glass-ceramic material is disclosed in the commonly assigned pending U.S. patent application Ser. No. 798,671. When a glass-ceramic coating is desired the devitrification may be effected either before or after the coating is applied to the substrate, according to known techniques. An implant comprising a e.g. borosilicate glass body or coating wherein the surface only of said body or coating has been leached to render said surface biologically active is within the scope of the present invention.

In another aspect of the present invention the bonding surface of a dental or surgical implant comprises any biologically compatible inorganic material, other than a silicon dioxide-based glass or glass-ceramic containing less than about 80 weight percent silicon dioxide (some of these being known), which is capable of developing a porous silica-rich surface layer having a specific surface area of at least about 80 square meters per gram within about 10 days' exposure according to the in vitro test described earlier. Such a material may be, for example, a hardened inorganic cement, a ceramic, a glass, a glass-ceramic, or fall within any other classification of inorganic material. The fact that in the case of Portland cement, for example, the surface layer developed in vivo contains significant amounts of other inorganic oxides (i.e., alumina and iron oxide) as well as silica, does not remove implants comprised thereof from within the scope of this invention. An example of a biologically compatible hardened inorganic cement is Portland cement, which has the composition (dry basis):

|  |  |
|---|---|
| $SiO_2$ | 20–24 weight percent |
| $Fe_2O_3$ | 2–4 weight percent |
| $Al_2O_3$ | 1–14 weight percent |
| CaO | 60–65 weight percent |
| MgO | 1–4 weight percent |

-continued

|  |  |
|---|---|
| $SO_3$ | 1–1.8 weight percent | and a specific surface area (hardened) of over 200 square meters per gram. The implant may e.g. be unitary or comprise a substrate of another material such as a non-biologically active ceramic, organic polymer, plastic or metal (e.g. Vitallium, trademark of Howmedica Inc., New York, N.Y.) coated with a biologically active material, e.g. a ceramic or cement. Processes known to the art for making unitary articles of cements, ceramics or other materials, or for coating substrate materials therewith, or for making any other configuration useful as an implant may be used in the practice of this aspect of the invention. When the implant comprises hardened inorganic cement, the hardening of the cement may occur before or after implantation. Thus, in one embodiment of the invention a bone replacement prosthesis is made by inserting wet cement into a cavity in the bone of the recipient formed by removal of diseased or damaged bone, molding the cement to the desired shape and then allowing the cement to harden in situ.

In still another aspect of the present invention a surgical or dental implant is bonded to bone by using a wet hardenable inorganic cement. The bonding surface of the implant, i.e. the surface in contact with said cement for bonding to the bone of the recipient, preferably comprises a biologically active silicon dioxide-based glass or glass-ceramic. The cement is one which, in the hardened state, is capable of developing a porous silica-rich surface layer having a specific surface area of at least about 80 square meters per gram within about 10 days' exposure according to the in vitro test described earlier. Because the cement develops the biologically active, high specific area, porous, silica-rich surface layer as it hardens in vivo, it forms a very strong bond with bone. It also forms a very strong bond with the biologically active glass or glass-ceramic surface of the implant, if such a surface is utilized. The hardened cement material is, of course, strong in its own right. Thus, the problems associated with the use of polymethylmethacrylate resin cements may be reduced, i.e., the problems of toxicity, loosening and reactivity in vivo. In another preferred embodiment the cement is reinforced with particles of a biologically active silicon dioxide—based glass or glass-ceramic, not only to increase its strength per se, but also to improve the respective strengths of the bone to cement and implant (when biologically active as described above) to cement bonds.

The following examples illustrate the invention but are not to be construed as limiting the same.

EXAMPLE 1

Implants of Thirsty Glass (Corning Glass Works, Corning, New York) of $4 \times 4 \times 1$ mm. were made and wet polished with 320 and 600 grit silicon carbide polishing discs. They were then ultrasonically cleaned in distilled water and sterilized by boiling. The Thirsty Glass sample used consisted of about 96 weight percent silicon dioxide and 4 weight percent boron oxide, and had a specific surface area of 200 square meters per gram, a porosity of 28 volume percent and an average pore diameter of 40 Angstroms. The implants were tested for bonding to bone in vivo by means of the rat tibial mini pushout procedure known to the art. No bonding was observed between bone and implants at either 11 or 18 days after implantation. After 40 days of implantation, however, two implants out of two passed the mini pushout test for bonding. One of these implants were sectioned, and microscopic examination showed that a direct chemical bond had formed between the Thirsty Glass implant and the healing bone.

EXAMPLE 2

The dry Portland cement used in this experiment was American Society for Testing Materials Type II Portland cement. Hardened samples were made by adding water to cement at a water to cement ratio of 0.4 and allowing the mix to harden for about two weeks to thirty days. After hardening, 4×4×1 mm. implants were fabricated from the cement. These were wet polished using 320 and 600 grit silicon carbide polishing discs. The implants were then rinsed in distilled water and allowed to remain in the rinse solution until implanted. In vivo testing for bonding to bone was performed using the rat tibial mini pushout procedure known to the art. No bonding was observed after 10 and 13 days implantation. After 28 days implantation, however, two samples out of two passed the mini pushout test for bonding. After 69 days implantation one sample out of one passed the mini pushout test. After 92 days implantation one sample out of one passed the mini pushout test. Qualitative mechanical testing of the implant-bone junction after 92 days showed fracture within the bone or the implant but not at the interface between the materials. Microscopic examination showed a direct chemical bond between the prehardened Portland cement implants and the healing bone.

What is claimed is:

1. A dental or surgical implant having a surface for bonding to the bone of a recipient, said bonding surface comprising a biologically compatible glass, glass-ceramic or ceramic material comprising at least about 80 weight percent silicon dioxide and having a specific surface area of at least about 80 square meters per gram, a porosity of from about 10 to about 50 volume percent, and an average pore diameter of from about 20 to about 300 Angstroms.

2. An implant of claim 1 wherein said material contains less than about 1 weight percent calcium and less than about 0.1 weight percent phosphorus.

3. An implant of claim 2 wherein said material comprises at least about 95 weight percent silicon dioxide.

4. An implant of claim 1 wherein said material comprises up to about 20 weight percent boron oxide.

5. An implant of claim 4 wherein said material is a glass.

6. A dental or surgical implant having a surface for bonding to the bone of a recipient, said bonding surface comprising a biologically compatible inorganic material capable of developing a porous silica-rich surface layer having a specific surface area of at least about 80 square meters per gram within about ten days' exposure to aqueous tris(hydroxymethyl)aminomethane buffer at a pH of 7.2 and a temperature of 37° C., said material being other than a silicon dioxide—based glass or glass-ceramic containing less than about 80 weight percent silicon dioxide.

7. An implant of claim 6 wherein said material is a hardened inorganic cement.

8. An implant of claim 7 wherein said cement is hardened Portland cement.

9. An implant of claim 6 wherein said material is a ceramic.

10. In a process for the fixation of a dental or surgical implant to bone comprising placing a wet cement between the surfaces of bone and implant and allowing said cement to harden, the improvement which comprises using a biologically compatible inorganic cement which, in the hardened state, is capable of developing a porous silica-rich surface layer having a specific surface area of at least about 80 square meters per gram within about ten days' exposure to aqueous tris(hydroxymethyl)aminomethane buffer at a pH of 7.2 and a temperature of 37° C.

11. The improvement of claim 10 wherein said cement is Portland cement.

12. The improvement of claim 10 wherein said wet cement is mixed with particles of a biologically active silicon dioxide—based glass or glass-ceramic.

13. The improvement of claim 10 wherein the bonding surface of said implant in contact with said cement comprises a biologically active silicon dioxide—based glass or glass-ceramic material.

* * * * *